United States Patent [19]
Santos

[11] Patent Number: 5,667,483
[45] Date of Patent: Sep. 16, 1997

[54] DENTAL DOUCHE

[76] Inventor: Vicente Laserna Santos, Virgen de Aranzazu 7-C1-1º A, Madrid, Spain, 28034

[21] Appl. No.: 386,923

[22] Filed: Feb. 10, 1995

[30] Foreign Application Priority Data

Feb. 12, 1994 [ES] Spain ................... 9401407-8
May 24, 1994 [ES] Spain ................... 9401431/0
Jul. 6, 1994 [ES] Spain ................... 9401882

[51] Int. Cl.$^6$ ........................................ A61G 17/02
[52] U.S. Cl. ........................ 601/162; 601/165; 433/80
[58] Field of Search ................. 433/80; 601/162, 601/165

[56] References Cited

U.S. PATENT DOCUMENTS

| | | | |
|---|---|---|---|
| 3,537,444 | 11/1970 | Garn et al. | 601/165 |
| 3,771,517 | 11/1973 | Radecki | 601/165 |
| 3,973,558 | 8/1976 | Stouffer et al. | 601/165 |
| 4,564,005 | 1/1986 | Marchand et al. | 601/165 |
| 4,941,459 | 7/1990 | Mathur | 601/165 |
| 4,942,870 | 7/1990 | Damien | 601/165 |
| 5,095,893 | 3/1992 | Rawden, Jr. | 601/165 |
| 5,218,956 | 6/1993 | Haadler et al. | 601/165 |
| 5,220,914 | 6/1993 | Thompson | 601/165 |
| 5,231,978 | 8/1993 | Kao et al. | 601/165 |
| 5,385,533 | 1/1995 | Coviello | 601/165 |
| 5,387,182 | 2/1995 | Otani | 601/165 |

*Primary Examiner*—Nicholas D. Lucchesi
*Attorney, Agent, or Firm*—Larson and Taylor

[57] ABSTRACT

An oral irragating device comprising three zones with pressurised water: having a jet, of individual character, and changeable, which can be screwed to a two-part stem which water is delivered to from a small flexible tube fitted directly to a tap with a suitable connection using a clamp and pressure screw to adjust to the tap opening, thereby avoiding leaks. A flexible strip can secure this mechanism to the tap. The tap connection may be a bowl pressed onto the tap.

4 Claims, 4 Drawing Sheets

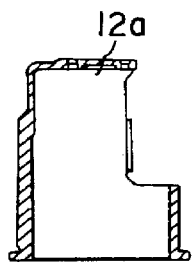 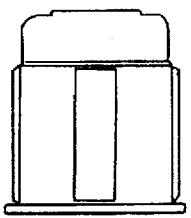 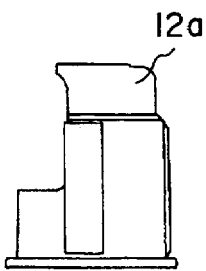 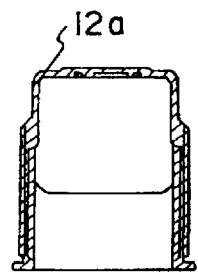
FIG.4a   FIG.4b   FIG.4c   FIG.4d
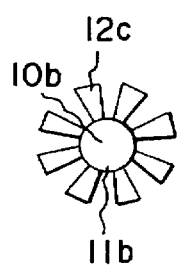 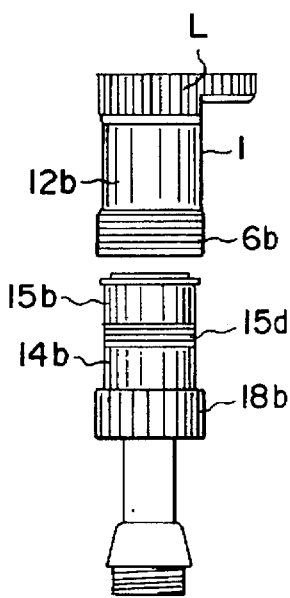 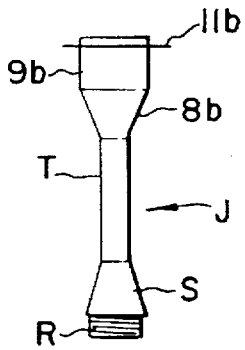 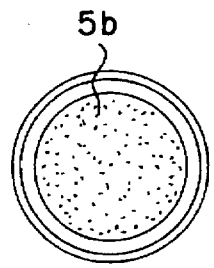
FIG.5   FIG.6   FIG.7   FIG.8
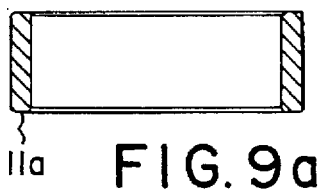
FIG.9a
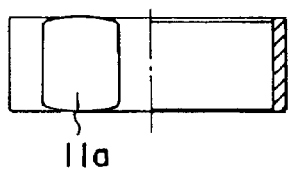
FIG.9b
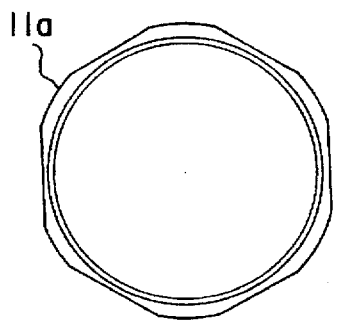
Fig.9c 5,667,483

DENTAL DOUCHE

BACKGROUND AND SUMMARY

This invention refers to an Oral Irrigating Device with a new system for cleaning teeth, the gingival groove (between gum and tooth) and the spaces between the teeth, using pressurized water, at the required temperature, to remove all remove all remains of food or residue.

The two-part design of the stem of this invention enables water to be mixed with anti-inflammatory and antiseptic medication and liquid dentifrice. In this process only the pressure of the tap water is necessary; in this way, hot and cold water may be mixed as required.

Given the simplicity of the system it is assumed that it will not be expensive to acquire and that maintenance costs will be zero.

In operation, it does not cause unpleasant sounds, and there are no risks involved in its use. After use, the cleaning of the Oral Irrigating Device may, because of its ease of assembly, even include its sterilization using chemical procedures (antiseptic products) or physical procedures (boiling water) so avoiding subsequent risks of infection. It is, thanks to its reduced size (little more than a toothbrush), easily transported.

Other dental cleaning mechanisms using pressurized water driven by electrical pumping devices already exist. However, the following difficulties arise with such electrical pumping devices:

They enable anti-inflammatory and antiseptic medicinal products to be mixed (but with greater potential for deterioration of the apparatus).

They are, because of their weight and size, difficult to transport.

With their electrical pumping devices, initial costs and maintenance are more expensive.

They are noisy.

There were also Oral Irrigating Devices on the market which connect directly to the tap, but they have the following defects:

They were hard to fit to the tap, freely losing water and, therefore, the pressure for cleaning the teeth.

If water pressure was too high, the Oral Irrigating Device would shoot off the tap and, if too low, it was insufficient to clean.

Water and medicinal products could not be mixed.

This new system for gum and tooth cleaning seeks to provide a new solution for good dental and gum conservation and health, as a complement to other forms of dental cleaning. It is of particular benefit to persons with special sensitivity to the friction of other mechanical cleaning procedures, those with periodontal disease (bleeding gums in diseases such as pyorrhea and gingivitis), apart from being of great utility to the whole family.

The benefits provided by this invention are revealed in the specifications although some of the most notable are described below, by way of illustration and without limitation:

Ease of assembly.

Ease of cleaning, so that it can be completely sterilized.

Economy of manufacture.

Medicinal products, such as antiseptics or anti-inflammatories can be mixed with the water.

Absence of noise.

With a change of jet, this device can be used as a vaginal douche.

BRIEF DESCRIPTION OF THE DRAWING

For a better grasp of these specifications, the attached drawings are included showing one design, without limitation, for the subject of this invention, in which:

FIGS. 4a, 4b, 4c, 4d are each a view from different sides of the tap fixture bowl from the design in FIG. 3.

FIG. 5 is a face view of the horizontal cross-section, at the top of the tube where it connects to the tap.

FIG. 6 is an exploded vertical view of another design for the tap fixture, with the different components situated vertically.

FIG. 7 is a vertical view of the tube.

FIG. 8 is a face view, from inside, of the upper base of the adaptor.

FIGS. 9a, 9b, 9c are each a face view and side elevation of the tap block nut in the design of FIG. 3.

DETAILED DESCRIPTION OF THE PREFERRED EMBODIMENTS

Figure 1:
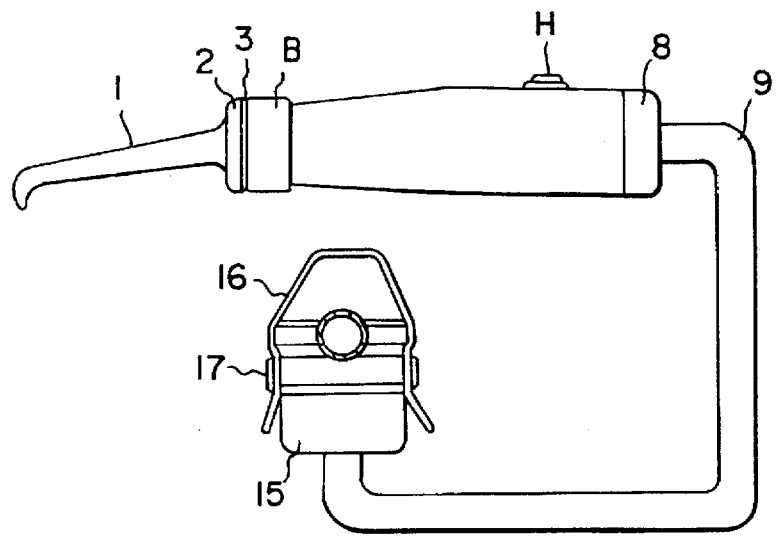
FIG. 1 shows a side view of the system, with the individual jet followed by the stem and the tap supply or connection system.
Figure 2:
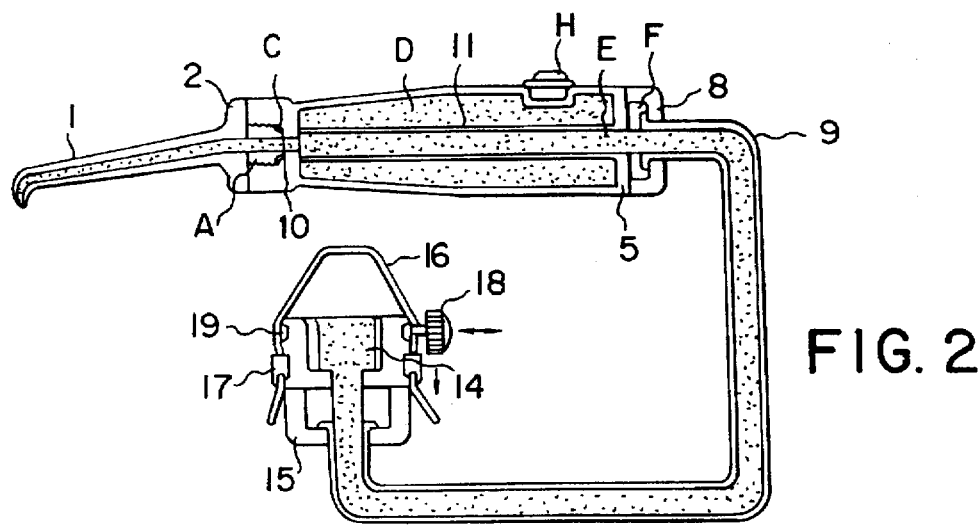
FIG. 2 shows a side view of the system for the feed or supply of fluid (water, liquid medication), with the concentric two-part (concentric bicameral) stem connected.

In line with the attached drawings, the Oral Irrigating Device as shown in FIGS. 1 and 2 consists of a jet (1) with a pouring tip (2) at a 90° angle, with a convex end. Said jet (1) is a shortened cone shape and is hollow, decreasing in diameter towards the end, with a washer (3) at the back to ensure its fit into the stem by means of a cylinder (A) which is axially hollow and threaded on the outside as shown in FIG. 2.

The end of the stem (B) which is also cylindrical is connected to said threaded cylinder (A) with the same diameter as the washer (3), with a hollow interior (C) also with an internal thread.

In the base of said thread, there is a seal or washer (10) to prevent water leaks.

Said stem is hollow, with an external chamber (D) (FIGS. 2, 3) along which there is a cylinder, likewise hollow, which forms the inside chamber (11).

On the sides of said internal chamber, very close to the ends, there are two holes (E) preferably of 0.2–0.4 mm diameter, aligned in opposite directions to facilitate the mixing of medicament or toothpaste in the outer chamber (D) with the water flowing through the inside chamber (11).

At the opposite end of the stem there is a cylinder with an external thread (F) to which an adaptor is screwed (8) which carries a flexible tube (9).

The stem (B) has a screw plug (H) over an opening through which the medicaments or liquid dentifrice are placed in the outer chamber of the stem.

Figure 19:
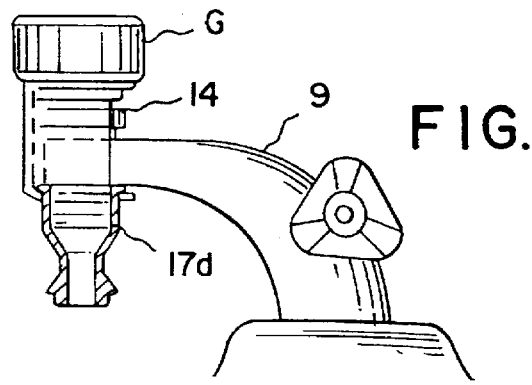
FIG. 19 is a side view of the connection secured to the tap.

The other end of the tube (9) has a bowl (14) inside a cylinder (15). Said bowl adapts to the tap (G) and is held in position with a strap (16) with two side fasteners (17) and a button (18) which presses on to a circular flange (19) to hold the bowl (14) on the tap (G) as shown in FIG. 19.

Water flows when the tap (G) (FIG. 3) is opened, first in the inside chamber (11), with a bore of about 8 mm then, through two facing holes (E) of 0.2–0.4 mm diameter, one distal and the other proximal, under pressure difference, from the internal to the external or surrounding chamber where pressure is lower. This enables dosing of the medication to be used (5 or 10 cc) which was inserted through the 0.5 cm hole on the furthest third of the outside of the stem through screw plug (H). Pressure then increases in the internal chamber as dissolution takes place, then flowing once more through the internal chamber (11), the liquid emerges through the jet, whose bore is of approximately 0.8 mm, in order, as designed, to clean gums and teeth while massaging the gums.

Pressure, water jet speed and temperature are adjusted using the tap opening and closing systems. Water is mixed with medication and emerges in the time usually employed in cleaning the teeth (2–3 minutes).

Figure 3:
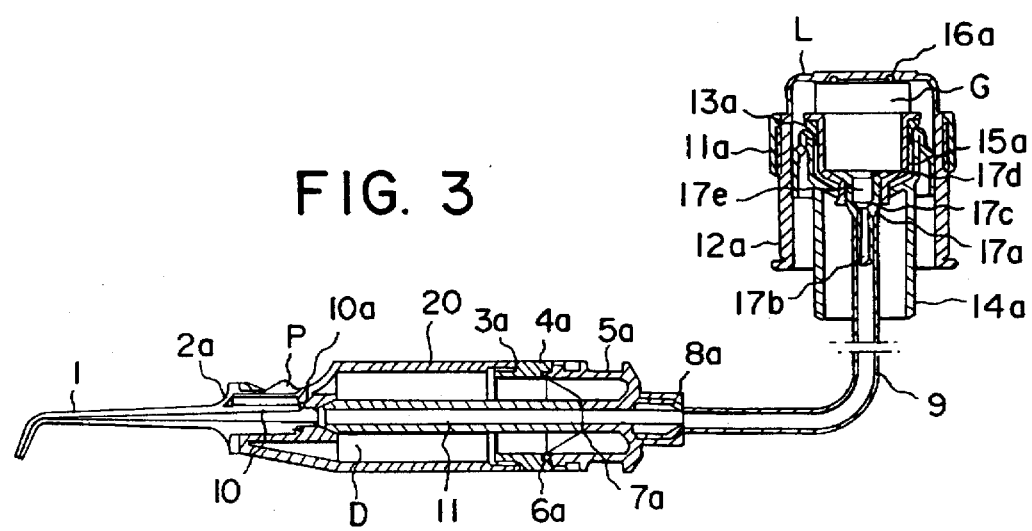
FIG. 3 shows a cross-section of the device with another design for the tap fixture.

In a design variant shown in FIG. 3, the jet (1) has an adaptor (2a) at its wider end with two or more ribs (P) on the sides which arch in concave form, pressing on the end of the housing until they fit into the housing where an O-ring (10a) is placed inside.

The casing (20) with an internal lengthwise duct, forming inside chamber (11) is stepped at the end opposite the jet. A further O-ring (3a) is fitted at the end opposite the jet on a mixing tube (4a) against which a seal is fitted (5a), each of which with an O-ring (6a and 7a) (FIG. 3) between the casing (20) and the outer chamber (D).

The seal ends with a nut (8a) on the tube (9) connected to the tap (G).

Figure 11:
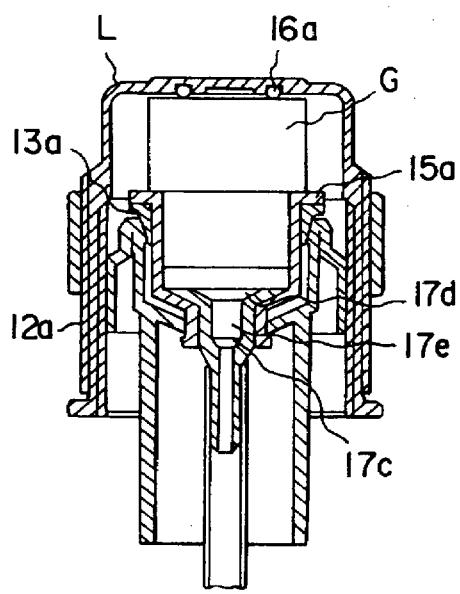
FIG. 11 shows a vertical cross-section view of the mechanism for connection to a high-level tap in the design in FIG. 3.
Figure 12:
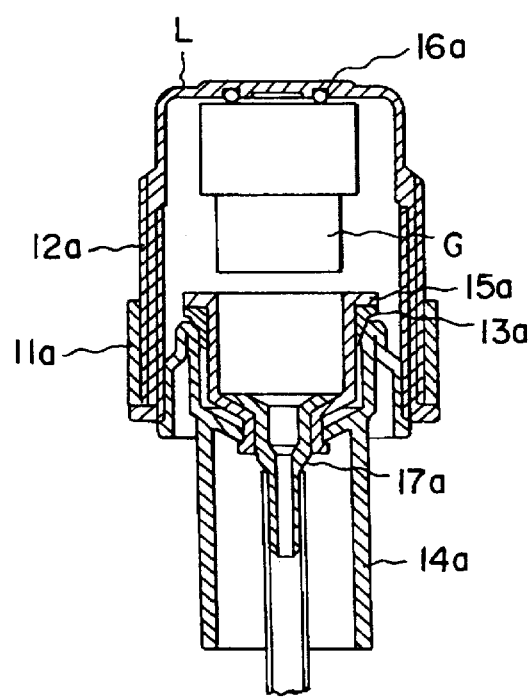
FIG. 12 shows a vertical cross-section of the mechanism for connection to a high level tap, fully opened.
Figure 13:
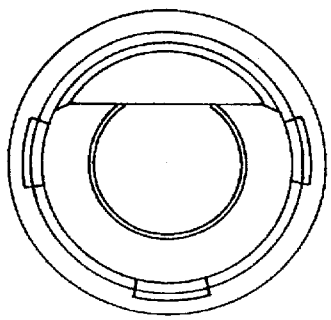
FIG. 13 shows a face view of the connecting bowl in the design in FIG. 3.
Figure 14:
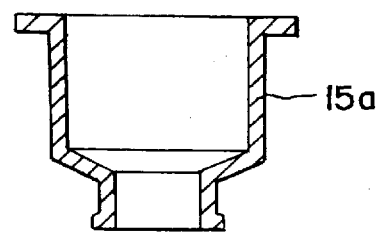
FIG. 14 shows a vertical cross-section of the bowl seal in the design in FIG. 3.
Figure 15A:
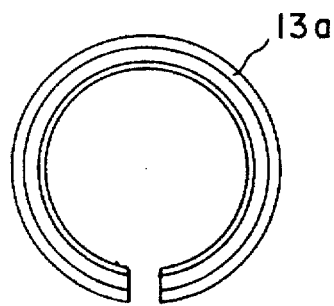
FIGS. 15a, 15b each show a face view and vertical cross-section of the elastic ring of the bowl connection in that design.
Figure 15B:
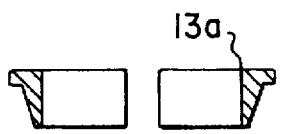
Figure 16:
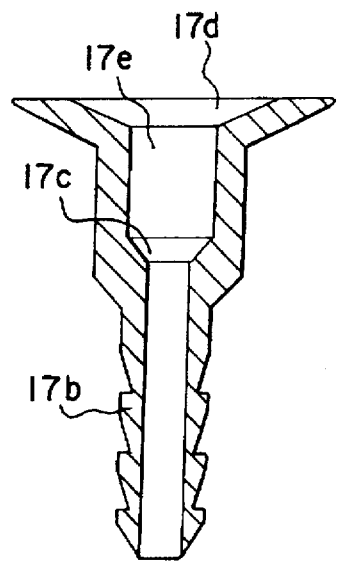
FIG. 16 shows a vertical cross-section of the shank connecting to the tube in the design in FIG. 3.

The tap attachment is shown in FIGS. 3, 11, 12 and consists of a shank (17a) fitted into the tube by its cylindrical tip (17b), the end of which is slightly tapered, with outside step-like indentations to ensure that it is secured against the inside of the tube. The other end of the shank (17a) has two shortened cone elements (17c and 17d) (FIGS. 3, 11, 16) separated by a cylindrical section (17e) (FIGS. 3, 11, 16) which fits into the bowl seal (15a) on the outside of which there is a flexible washer (13a) shown in FIGS. 3, 11, 12, 15) around the widest section of the bowl (14).

Figure 10A:
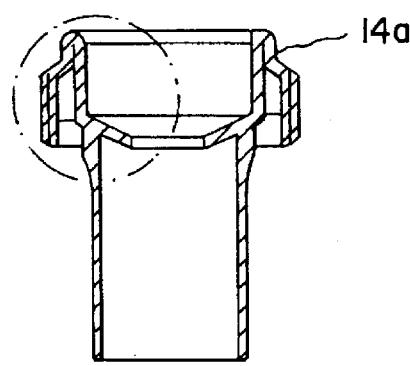
FIGS. 10a, 10b are each a vertical cross-section and side elevation of the plunger, according to the design in FIG. 3.
Figure 10B:
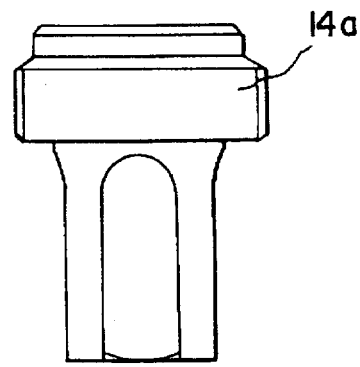

The tap connection has a plunger (14a), shown in FIGS. 3, 10, 12, inside the bowl housing (12a), shown in FIGS. 3, 4, 11, 12 in which, the cylindrical seal (15a) (FIGS. 3, 11, 12, 14) is fitted. The tap (G) is inserted here and is pressed against it by means of the flexible washer (13a). There is an O-ring (16a) (FIGS. 3, 11, 12) at the top of the tap.

A securing nut (11a) (FIGS. 3, 9, 12) surrounds the bowl.

In another design, the adaptor (FIG. 6 consists of an inverted cylindrical bowl (12b) made of some suitable material such as plastic, with a side opening (I) into which the tap is inserted.

The upper base (L) shown in FIGS. 3, 6, 11, 12 of the bowl is closed by a cover with a disc (5b), as shown in FIG. 8, on the inside made of plastic providing a seating and/or seal when the tap is pressed, at the same time as preventing damage to it. The lower base of the bowl is open and the side, close to the base, has spiral ribbing (6b) (FIG. 6) around the outside.

FIG. 7 shows that the adaptor bottom, which fits into the bowl (12b), consists of a shaft (J) formed by the tube (T) which widens at the top to form an initial section in shortened cone shape (8b) and a further cylindrical section outside (9b). The external radial opening of (10b) shown in FIG. 5 of shaft (J) shown in FIG. 7 has a washer (11b) (shown also in FIG. 5) with tapered fingers (12c) diverging radially and designed to reinforce the pressure-fit of the tube on the tap.

The opposite end of the tube (T), is a widened shortened cone (S) terminating in a hollow cylinder (R) of larger diameter than the wider base of said shortened cone, and with outside ribbing.

FIG. 6 shows a washer (15b) which surrounds the tube (T) and has small vertical external protrusions and is linked to a hollow cylinder (15d). The hollow cylinder (15d) has external ribbing, onto which a washer (14b) is screwed with internal ribbing. Washer (14b) has small vertical protrusions in which to fit a last washer (18b) of greater diameter which acts as a component to press and secure the assembly.

Figure 17:
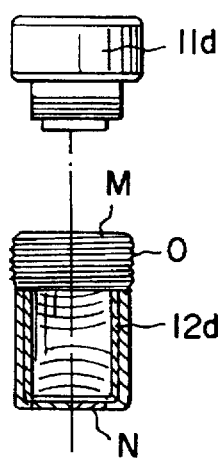
FIG. 17 shows a vertically exploded view of the tap connection, threaded at the top, according to another design.
Figure 18A:
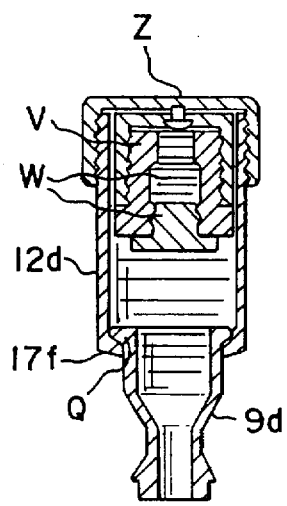
FIGS. 18a, 18b, 18c each show a cutaway view in perspective of the tap connection in said other design, with the thread at the top.
Figure 18B:
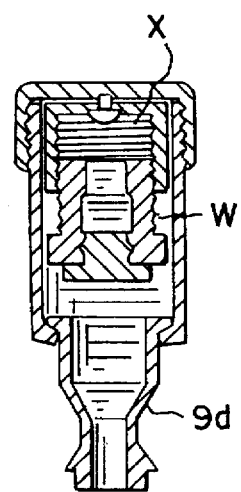

In another design, the connection (14) (FIGS. 2 and 19) may be screwed onto the tap (G) at the top, as shown in FIGS. 17, 18 and 19, according to which this design consists of three parts.

FIG. 17 shows a hollow cylinder (12d) which may be transparent, as shown, with a hole at the top (M) which is larger than the one at the bottom (N).

The top of the cylinder has an outside thread (O) to fit the pressure plug (11d).

The pressure plug (11d) is the second element comprising the system.

The third part is shown in FIG. 18a,b as a tube (9d) with circular ribs (Q) at the top to allow it to fit against the rib (17f) in the bottom of the hollow cylinder so as to connect them. Once circular rib (Q) is pressed against the rib (17f), the water pressure ensures that they do not move. As a result, the tube is perfectly adjusted to the lower opening (N) of the hollow cylinder.

The pressure the screw or cover (11d) consists of four parts in this design.

Figure 18C:
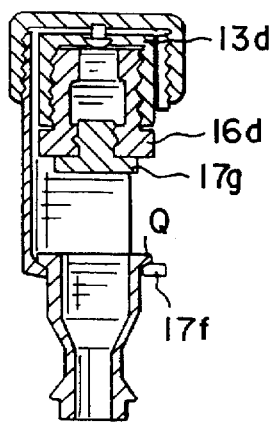

FIG. 18 shows they cylindrical cover (11d) with an inside thread for adjustment to the hollow cylinder of the capsule (12d). The top of the plug (13d) (FIG. 18c) has a hole in the middle (Z) (FIG. 18a) for a screw to link it to the inside cylinder of the plug (13d).

The inside cylinder of the plug (13d) is the second element and is open at the bottom. Inside, the cylinder is also threaded for a screw (W) of the same diameter and with a screw top (16d) inside.

The inside screw (W), which is also cylindrical and hollow, enables the plug (13d) to be lengthened, if necessary, up to almost one third of its total, in order to adapt to different tap models.

The inside screw (W) has a rubber cylinder (17g) linked to it with an outside head of greater diameter which contacts with the tap to prevent movements and damage to the tap (G), and it is to this element (G) that pressure is applied when the plug (13d) is screwed up, fitting the tube (9) against the opposite side of the tap. This compresses the rubber cylinder head against the side of the opening and against the tap, preventing leakage of water or other fluids.

When tightened, the external cover (11d) directs force downwards but not sideways, so maintaining the distance to which the internal lengthening screws (W) were set.

FIG. 19 shows the adaptor unit in this last design, connected to the tap, shown in trace form.

To connect the adaptor in this last design, the plug is completely unscrewed and the tube placed in the mouth of the tap which was inserted through the side opening. Hold with one hand and insert the plug with the other, screwing it up tight so as to completely fit the tube by the traction on the opposite side. This compresses the tube which is pressed against the opposite side of the mouth and against the tap thanks to the elasticity of the rubber, so preventing leaks.

It will be almost impossible to move the apparatus forward except in the case of some taps of unusual design.

The assembly as a whole is encased so that any fortuitous leaks when the tap is opened will hardly ever be a nuisance to the user nor cause any loss of pressure.

I claim:

1. An oral irrigating device comprising:

a jet having a convex end and a pourer tip at 90 degrees with said convex end, said jet having a shortened cone-shape tapering towards said convex end;

a back end of said jet having a washer acting as a stop for adjusting said back end relative to a stem, said back end of said jet linking said jet to an axially hollow and externally threaded cylinder, said stem having a top, a back end, and a screw plug, said stem top being threadedly fitted into said threaded cylinder;

said stem having a hollow cylinder therein forming an outer chamber and an inner chamber, said inner chamber having two holes, wherein the back end of said stem has an externally threaded stem cylinder to which an adaptor is screwed and which carries one end of a flexible tube, said tube having another end connected to a bowl, said bowl having a strap, two sides with two fasteners on said sides, and a button to tighten a circular flange that secures said bowl on a tap which supplies irrigating fluid to said device.

2. An oral irrigating device as in claim 1, wherein the jet terminates at a widest part in an adaptor having at least one rib of arched concave shape, wherein said stem cylinder terminates at an end opposite the jet in a step where a first O-ring is fitted on a mixing tube against a seal having a second O-ring in the stem cylinder, said seal ending in a nut secured on to said tube; wherein the tap comprises a shank which fits into the tube at one end and the other end of said tube has two shortened cone shaped components separated by a cylindrical section fitted into the seal of the bowl, wherein a plunger is fitted into the bowl where the shortened cone shaped components are fitted into an end of the tap.

3. An oral irrigating device as in claim 1, wherein the adaptor comprises an inverted cylindrical bowl, an upper base closed by a cover with a plastic disc inside, an open lower base having spiral ribbing around an outside portion, and a bottom wherein the bottom of the adaptor comprises a shaft including a second tube which-widens at an upper end to form a first section of a shortened cone shape with a further external cylindrical section whose external radial opening has a washer with radially divergent tapered fingers, said second tube further terminating at an opposite end in a diverging shortened cone culminating in a hollow cylinder, said second tube has a washer which surrounds the second tube, and small vertical projections being disposed of on an outside of said second tube and being connected to a hollow cylinder having outside ribbing onto which a ribbed washer is screwed.

4. An oral irrigating device as in claim 1 further comprising a hollow top cylinder having a top, bottom and a hole at a top said hollow tap cylinder and being larger at said top than at said bottom, than that at a bottom said top having an external thread connected to a pressure plug, wherein said pressure plug comprises a cylindrical cover having a connection to said plug, an internal cylinder of the plug being open at a cylinder bottom and threaded for an inside screw, said inside screw having an inside screw diameter, a rubber cylinder having an external screw head of diameter greater than said inside screw diameter and being connected to said inside screw.

* * * * *